United States Patent
Candido et al.

[11] Patent Number: 5,877,398
[45] Date of Patent: Mar. 2, 1999

[54] BIOLOGICAL SYSTEMS INCORPORATING STRESS-INDUCIBLE GENES AND REPORTER CONSTRUCTS FOR ENVIRONMENTAL BIOMONITORING AND TOXICOLOGY

[75] Inventors: Edward Peter Mario Candido; Eve Gabrielle Stringham, both of Vancouver; Donald Jones, Burnaby, all of Canada

[73] Assignee: University of British Columbia, British Columbia, Canada

[21] Appl. No.: 418,531

[22] Filed: Apr. 7, 1995

Related U.S. Application Data

[63] Continuation of Ser. No. 10,828, Jan. 29, 1993, abandoned.
[51] Int. Cl.$^6$ .............................. C12N 5/00; C12N 15/00; G01N 33/53
[52] U.S. Cl. ...................... 800/2; 800/DIG. 1; 424/9.2; 435/975; 436/815
[58] Field of Search ................... 800/2, DIG. 1; 424/9.2; 435/172.3, 975; 536/23.2, 24.1; 935/59; 436/183, 815

[56] References Cited

U.S. PATENT DOCUMENTS

| | | | |
|---|---|---|---|
| 4,345,026 | 8/1982 | Lew | 435/4 |
| 4,444,891 | 4/1984 | Miwa et al. | 436/2 |

FOREIGN PATENT DOCUMENTS

| | | |
|---|---|---|
| 118 393 | 9/1984 | European Pat. Off. . |
| 263 908 | 4/1988 | European Pat. Off. . |
| 336 523 | 11/1989 | European Pat. Off. . |
| WO 87/05935 | 10/1987 | WIPO . |
| WO 90/02947 | 3/1990 | WIPO . |
| WO 90/04037 | 4/1990 | WIPO . |
| WO 90/13028 | 11/1990 | WIPO . |

OTHER PUBLICATIONS

Stringham and Candido, "Use of Transgenic Strains of The Nematode *Caenorhabditie elegans* as Biological Monitors of Environmental Stress," in *SETAC 92, Abstracts of the 13th Annual Meeting of the Society of Environmental Toxicology and Chemistry*, Nov. 8–12, Cincinnati, 1992, p. 10, Abstract No. 91.

Williams et al., "Using the Nematode *Caenorhabditis elegans* to predict mammalian acute Iethality to Metallic Salts," *Toxic and Industrial Health* 4: 469–478, 1988.

(List continued on next page.)

*Primary Examiner*—Bruce R. Campbell
*Attorney, Agent, or Firm*—Seed and Berry LLP

[57] ABSTRACT

A method and kit for detecting toxins and pollutants is disclosed. The kit includes a transgenic organism having a stress-inducible control region linked to a gene encoding a detectable protein wherein said control region regulates the expression of said detectable protein; exposing said organism to said sample; and determining the amount of detectable protein produced. Exposure of this organism to a toxin or pollutant induces the production of the detectable protein which can be easily measured. This invention provides a rapid and reliable system for testing samples for the presence of toxins or pollutants.

9 Claims, 8 Drawing Sheets

OTHER PUBLICATIONS

Williams et al., "Aquatic Toxicity Testing using the Nematode, *Caenothabditits elegans*," *Environmental Tox. and Chem.* 9: 1285–1290, 1990.

Stringham et al., "Temporal and Spatial Expression Patterns of the Small Heat Shock (hsp16) Genes in Transgenic *Caenorhabditis elegans*," *Mol. Biol. Cell.* 3: 221–233, 1992.

Stringham and Candido, "Transgenic hsp 16–lacZ Strains of the Soil Nematode *Caenothabditis elegans* as Biological Monitors of Environmental Stress," *Environmental Toxicology and Chemistry* 13(8): 1211–1220, 1994.

Stringham and Candido, "Targeted Single–Cell Induction of Gene Products in *Caenorhabditis elegans:* A New Tool for Developmental Studies," *Journal of Experimental Zoology* 266: 227–233, 1993.

Sanders, B., "Stress Proteins in Aquatic Organisms: An Environmental Perspective," *Critical Reviews in Toxicology* 23(1): 49–75, 1993.

Guven et al., "Evaluation of a stress–inducible transgenic nematode strain for rapid aquatic toxicity testing," *Aquatic Toxicology* 29: 119–137, 1994.

Fire et al., "A modular set of lacZ fusion vectors for studying gene expression in *Caenorhabditis elegans*," *Gene* 93: 189–198, 1990.

Fire, A., "Integrative transformation of *Caenorhabditis elegans*," *EMBO Journal* 5(10): 2673–2680, 1986.

Translational Fusions (Complete):

Translational Fusions (Exon 1):

Transcriptional Fusions:

BIOLOGICAL SYSTEMS INCORPORATING STRESS-INDUCIBLE GENES AND REPORTER CONSTRUCTS FOR ENVIRONMENTAL BIOMONITORING AND TOXICOLOGY

This application is a continuation of U.S. patent application Ser. No. 08/010,828, filed Jan. 29, 1993, abandoned.

FIELD

The effects of environmental conditions or toxicological agents on multicellular organisms are usually assessed by exposing a test organism (a biomonitor) in the environment or condition of interest, and then analyzing some biological parameter such as viability, reproductive success, or the level of some metabolite or enzyme. Alternatively, the same parameters may be measured on natural organisms already present in the environment. Such assessments typically are complex, lengthy and laborious: the culturing, exposure and assessment of the test organism requires many manipulations. This invention describes: 1) the use of transgenic organisms to monitor environmental effects or toxicity; 2) transgenic strains of the nematode, Caenorhabditis elegans, which respond to environmental conditions by producing an easily measured protein product; 3) methods and compositions for exposing the organism to test substances; 4) methods and compositions for readout of the organism's response.

I. BACKGROUND

The need for methods of assessing the impact of environmental pollutants on ecological systems has led to the development of procedures which utilize living organisms as biological monitors. The simplest and most convenient of these systems utilize unicellular microorganisms, since they are most easily maintained and manipulated.

Unicellular organisms, however, are inadequate models for estimating the potential effects of pollutants on complex multicellular animals, as they do not have the ability to carry out biotransformations. Biotransformations of chemical compounds by multicellular organisms is a significant factor in determining the overall toxicity of agents to which they are exposed. This fact has stimulated the search for model organisms in the latter category which could serve as biomonitors. The nematode, Caenorhabditis elegans, has become a widely used model system for genetic and molecular biological studies, and the ease of culture and handling of this organism has lead to the proposed use of this and related species as biomonitors in various applications. Some examples from the recent literature are:

1. Williams, P. L. and Dusenbery, D. B. "Using the nematode Caenorhabditis elegans to predict mammalian acute lethality to metallic salts." Toxicol. Ind. Health 4(4), 469–478, 1989.
2. Williams, P. L. and Dusenberry, D. B. "A promising indicator of neurobehavioral toxicity using the nematode Caenorhabditis elegans and computer tracking". Toxicol. Ind. Health 6(3–4), 425–440, 1990.
3. Williams, P. L. and Dusenbery, D. B. "Aquatic toxicity testing using the nematode, Caenorhabditis elegans". Environ. Toxicol. Chem. 9, 1285–1290, 1990.
4. Samoiloff, M., "The nematode toxicity assay using Panagrellus redivivus". Toxic. Assess. 5(3), 309–318, 1990.
5. Van Kessel, W. H. M., Brocades Zaslberg, R. W. and Seinen, W. "Testing environmental pollutants on soil organisms, using cadmium chloride and nematodes". Ecotoxicol. Environ. Saf. 18 (2), 181–190, 1989.

Over the last 15 years or so, it has been established that all organisms respond to heat stress and to a variety of chemical stresses by producing specific proteins which are made either at much lower levels or not at all under normal conditions. This realization has led to proposals for monitoring the environment by measuring the levels of these proteins in various organisms (1,2,3). These approaches involve extraction of the proteins and measurement of their levels, usually using antibodies.

The invention described herein utilizes a different approach, i.e, we have linked the control regions which regulate stress protein production to a gene which produces a readily measurable enzyme (a "reporter gene"). This reporter gene has been inserted into the chromosomes of C. elegans to produce transgenic strains which respond to stress by making the reporter enzyme. To complete the biomonitor system, methods have been designed for rapidly and conveniently assessing the magnitude of the reporter enzyme activity, as well as its tissue location in the nematode. The recombinant strains, together with the assay methodology, can constitute a biomonitoring "kit" which can be used to detect the level of stress imposed on an organism by exposure to water samples (salt or fresh water), sludges, sediments, soils, soil extracts, pesticides, etc.

II. SUMMARY OF THE INVENTION

1. The reporter genes.

The first in a series of stress gene-reporter constructs currently in use consist of the E. coli gene, lacZ, coupled to a stress-inducible promoter derived from the hsp16 gene of the nematode Caenorhabditis elegans LacZ encodes the enzyme, β-galactosidase, which is stable in nematode cells, and for which sensitive histological and spectrophotometric assays already exist.

Figure 1:
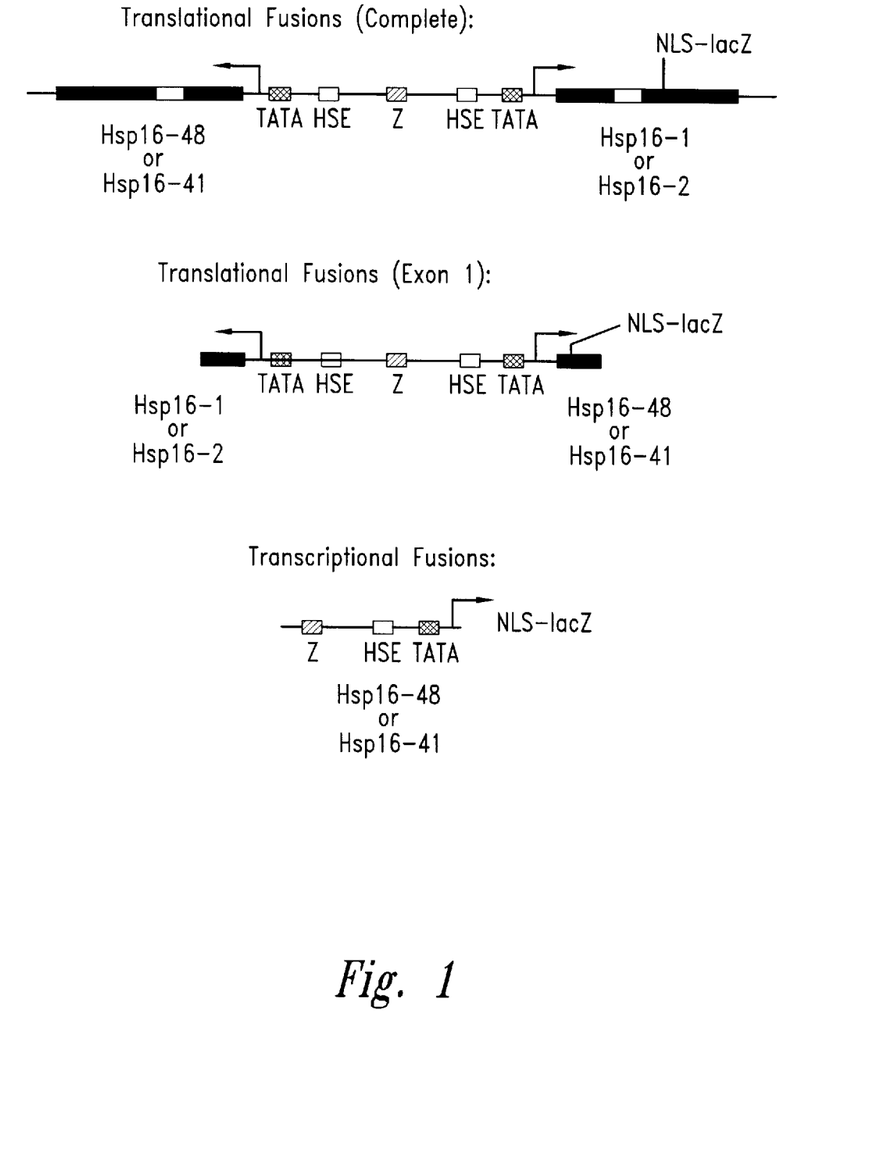

An advantage of these reporters is that the promoters are tightly regulated, i.e, little or no gene activity is present unless the animal has been stressed in some way, and the nematode possesses no β-galactosidase activity of its own. This means that background activity in the assays is extremely low, and that the assay is very sensitive. A schematic diagram of specific reporter genes which have been constructed is shown in FIG. 1. NLS, a nuclear localization signal, targets the β-galactosidase to the nucleus, making identification of the stressed cell and tissue types possible. HSE is a heat shock or stress inducible regulatory element. These vectors have been described in Stringham et al. (4). The complete sequences of the hsp 16 genes are described in Russnak et al. (5) and Jones et al. (6).

Other types of reporters which satisfy the above criteria are also consistent with this methodology. For instance, bacterial or firefly luciferase might be used to provide a sensitive assay based on photon emission (7). Any gene product for which the substrates can diffuse into the nematode cells in the procedure described below, would by compatible with this biomonitor system. Other promoters, which respond to different classes of stressors or conditions, could also be used in conjunction with the various reporter genes, e.g. metallothionein or cytochrome P450 promoters, or other heat shock promoters.

BRIEF DESCRIPTION OF THE DRAWINGS

FIG. 1. Reporter gene constructs which respond to environmental stressors (4). The complete translational fusion consists of a complete hsp16-4811 gene pair, including the 5' and 3' non-coding sequences of both genes, with the *E. coli* lacZ gene inserted in-frame into a unique HpaI site in the second exon of hsp16-1. The homologous construct uses the hsp16-4112 gene pair. The exon 1 fusions were constructed by cloning a Sau3A fragment containing the intergenic sequence of hsp16-4811, hsp 16- 1148 and hsp16-2141, respectively, into the EamHi site of the *lacZ* expression vector pPD16.51 (8). The arrows indicate the direction of transcription. Z represents an alternating purine-pyrimidine oracl. Transcriptional fusions removed the HSEs and TATA boxes of the hsp16-1 and hsp16-2 genes, respectively, but retained a single promoter (hsp16-48 or hsp16- 41). NLS, SV40 nuclear localization signal.

FIG. 2. Estimation of reporter gene copy number in transgenic strains. Serial two-fold dilutions of genomic DNA from PC73, PC72, PC71 and wild-type (N2) *C. elegans*, starting at 300 ng (0.3 µg), were spotted onto a nitrocellulose filter. For comparison, dilutions of the cloned *E. coli* lacZ gene, encoding β-galactosidase, were spotted along the bottom. The filter was then hybridized with a 32p-labelled fragment of lacZ DNA, and exposed to X-ray film. The loadings of lacZ DNA were chosen to represent 100, 50, 25 etc. copies of the gene in a 3 µg sample of nematode DNA. Thus a signal in the experimental genomic DNA samples must be multiplied by 10 (to allow for the difference in DNA loadings between the experimental points and the standards), and divided by two (to convert to haploid genome equivalents) to make it comparable to the standards. In practice the signals were quantified by densitometry, a standard curve was constructed, and the experimental values were determined from the standard curve. Note the absence of lacZ signal in the wild-type DNA.

FIG. 7. ONPG assay of strain PC71 exposed to cadmium chloride for 16 to 96 h. Aliquots of the nematodes were exposed to the agent in a multiwell plate, then processed in disposable centrifuge tubes. For each curve, the arithmetic means of three data sets were plotted. The 24 h and 48 h LC50 values are indicated by the vertical lines (11).

FIG. 8. In situ histochemical stain for α-glycerophosphate dehydrogenase (GPDH) in wild-type *C. elegans*. Nematodes were stained for GPDH after a 1 minute treatment with acetone. The staining mixture contained: 100 µl of Bovine Serum Albumin (10 mg/ml), 100 µl of NAD (10 mg/ml), 100 µl of Tric-HCl (1M, ph 8.5), 200 µl of a saturated solution of Nitro Blue Tetrazolium, 100 µl of α-glycerophosphate (2M), 20 µl of Phenazine methosulfate (1 mg/ml) and 1.0 ml of water. The incubation was at room temperature for 10 min. A control essay was carried out in which the substrate, α-glycerophosphate, was omitted. The control worms stained a light pink color, while those incubated in the complete mix stained a dark purple. After staining, both groups of worms were mixed together and photographed. Arrows indicate examples of GPDH stained worms, C indicates controls.

DETAILED DESCRIPTION OF STRESS-REPORTER GENE CONSTRUCTIONS (ALSO SEE (4))

The vector pPCZ1, illustrated in FIG. 1 as the hsp16-48/1 translational fusion complete, was constructed by inserting a 3500 bp HindIII-AflII fragment encompassing the lacZ gene (nucleotides 18 to 3518 of the expression vector pPD16-43 (B)) into the Hpa I site (nucleotide 3565 of the published sequence) of the hsp16-1 gene. pPCZ1 contains a complete hsp16-4811 gene pair extending from a Bcl I site at nucleotide 2280 to the Bam HI site at nucleotide 4186 in the published sequence (5). Plasmid pDX16.31 represents the complete translational fusion between lacZ and the hsp16-4112 gene pair, which was constructed by inserting lacZ as a 3200 bp XbaI-StnI fragment into the Hpa I site of hsp16-2 (nucleotide 1690, (6)). The latter was contained in an Eco RI (nucleotide 540) to Mbo I (nucleotide 2870) fragment encompassing the hsp16-4112 gene pair.

Plasmid pPC16.48.1, which corresponds to the translation exon 1 fusion of the hsp16-4811 gene pair to lacZ, was constructed by inserting a Sau 3A fragment extending from nucleotides 987 to 1440 (5) into the Bam HI site of the nematode expression vector pPD16.51 (8), such that the hsp16-48 promoter was proximal to lacZ. pPC16.1-48 contains the Sau 3A fragment in the inverse orientation such that the hsp16-1 promoter is closest to lacZ. A Sau 3A fragment extending from nucleotides 1121 to 1561 of the hsp16-4112 locus was cloned into the Bam HI site of pPD16.51 (8) such that the hsp 16-41 promoter was proximal to lacZ, generating plasmid pHS16.25 (illustrated as the translational exon 1 fusion of the hsp16-4112 gene pair).

Plasmid pPC16.48-51 is a transcriptional fusion consisting of an Mnl 1 fragment (nucleotides 3085 to 3262) of the hsp16-48 promoter cloned into the Hincil site of the pPD16.31 polylinker. pPC16.41-51 is a transcriptional fusion consisting of a Taq I fragment extending from nucleotides 1169 to 1409 in the hsp16-41 gene inserted at the Acc I site of pPD16.51. All of these gene constructions are described in Stringham et al. (4).

2. The strains

Initially, transgenic strains carrying extrachromosomal arrays of the hsp16-lacZ transgenes described in the preceding section were constructed and extensively characterized with respect to their induction by heat shock (4). In these strains, the introduced transgenic DNA was not integrated into the host genome but rather was carried as extrachromosomal arrays which were not passed to the next generation with 100% fidelity (4). While these strains produced large amounts of β-galactosidase in response to heat stress, no enzymatic activity was detected after the animals had been exposed to cadmium (4). Thus, we concluded at the time that the hsp 16 genes were not metal inducible genes (4).

Figure 2:
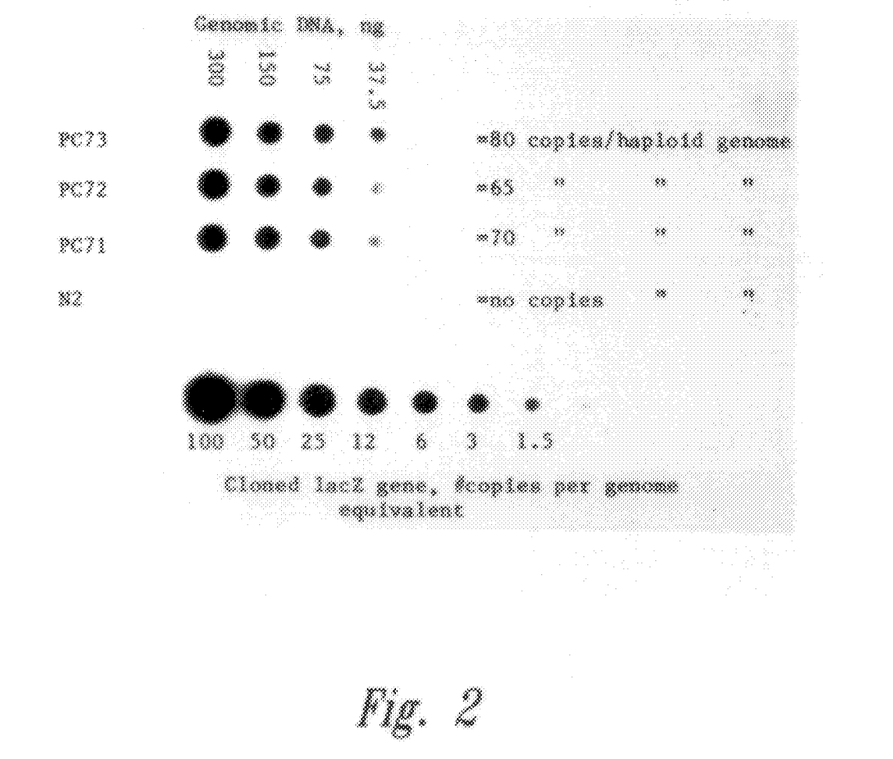

The transgenic nematode strains currently in use were produced by integrating the above reporter genes into the genome (9). Unexpectedly, these strains produce β-galactosidase in response to a variety of stressors, including cadmium, and heat stress (10,11). These strains are genetically stable, and were derived from the earlier, unstable strains described in Stringham et al. (4), by gamma irradiation and genetic selection for animals which passed on the transgene in 100% of their progeny (9). Genetic stability is an advantageous feature of this invention. In addition to the reporter gene of interest, these particular strains also carry a marker gene which results in a distinct pattern of movement of these animals, distinguishing them from the wild-type organism. Strains PC71 and PC72 carry the complete translational fusion shown at the top of FIG. 1. Strain PC73 carries the hsp16-48/1 translational exon 1 fusion shown in the middle of FIG. 1. The copy number of these reporter transgenes is estimated at 65–80 per haploid genome (FIG. 2). The transgenic nematodes PC71, PC72, and PC73 were deposited with the American Type Culture Collection, P.O. Box 1549, Manassas, Va. 20108-1549 on Oct. 1, 1997 and accorded the accession designations 209318, 209319, and 209320, respectively.

3. Exposure of the transgenic organisms to test materials (Refer to FIG. 3 and Reference II for detailed methods).

1. Use of test tubes or multiwell dishes.

Figure 3:
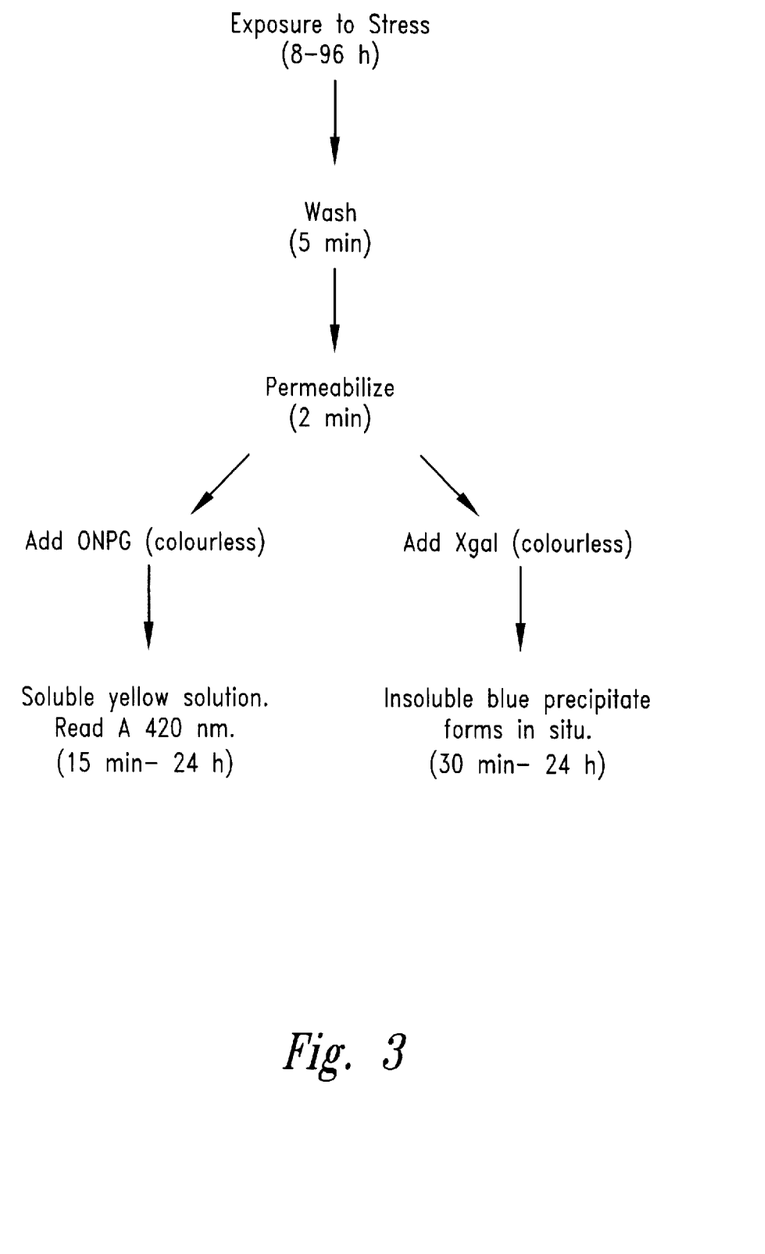
FIG. 3. Flow chart of the stress assay using transgenic *Caenorhabditis elegans* strains carrying stress-inducible promoters linked to *E. coli* β-galactosidase.

Thousands of transgenic L2 or L3 staged larvae can be cultured and exposed to test samples in multiwell tissue culture dishes in storage medium containing a lac-strain of *E. coli* as a food source (FIG. 3). In this fashion, numerous samples can be tested simultaneously, and the concentration or time of exposure to the test substance varied. This procedure also allows monitoring of the general health of the animals during the course of an experiment by observation with a dissecting microscope. At the completion of the exposure to the test substance the animals are transferred to a test tube, pelleted by centrifugation, washed briefly with distilled water, permeabilized with acetone and assayed for β-galactosidase activity by one of the two methods described below (FIG. 3). Alternatively, tissue culture dishes containing porous removable inserts which are acetone resistant would eliminate any requirement for test tubes and centrifugation. In a soluble assay, β-galactosidase cleaves the colourless substrate ONPG to release a soluble yellow product, ortho-nitrophenol, which has an absorbance maximum at 420 nm under basic conditions. Using this approach the magnitude of the response can be quantified spectrophotometrically. Alternatively, addition of the histochemical substrate Xgal results in the formation of an insoluble blue precipitate in situ, thus providing qualitative information as to the tissue distribution of the response (FIG. 3).

2. Soil testing.

The above procedure need only be modified slightly to test soil or sediment samples. A dense slurry containing the nematodes and a lac-strain of *E. coli* is added to 1–2 g of soil or sediment which is contained within a well of a tissue culture dish or a scintillation vial. Upon completion of the exposure, distilled water is added to the soil so that the animals float to the top for removal. The retrieved animals are washed, floated on 30% sucrose to remove remaining soil and bacteria (12), and assayed for β-galactosidase as described above.

3. A self-contained exposure and test chamber (STC).

Figure 4:
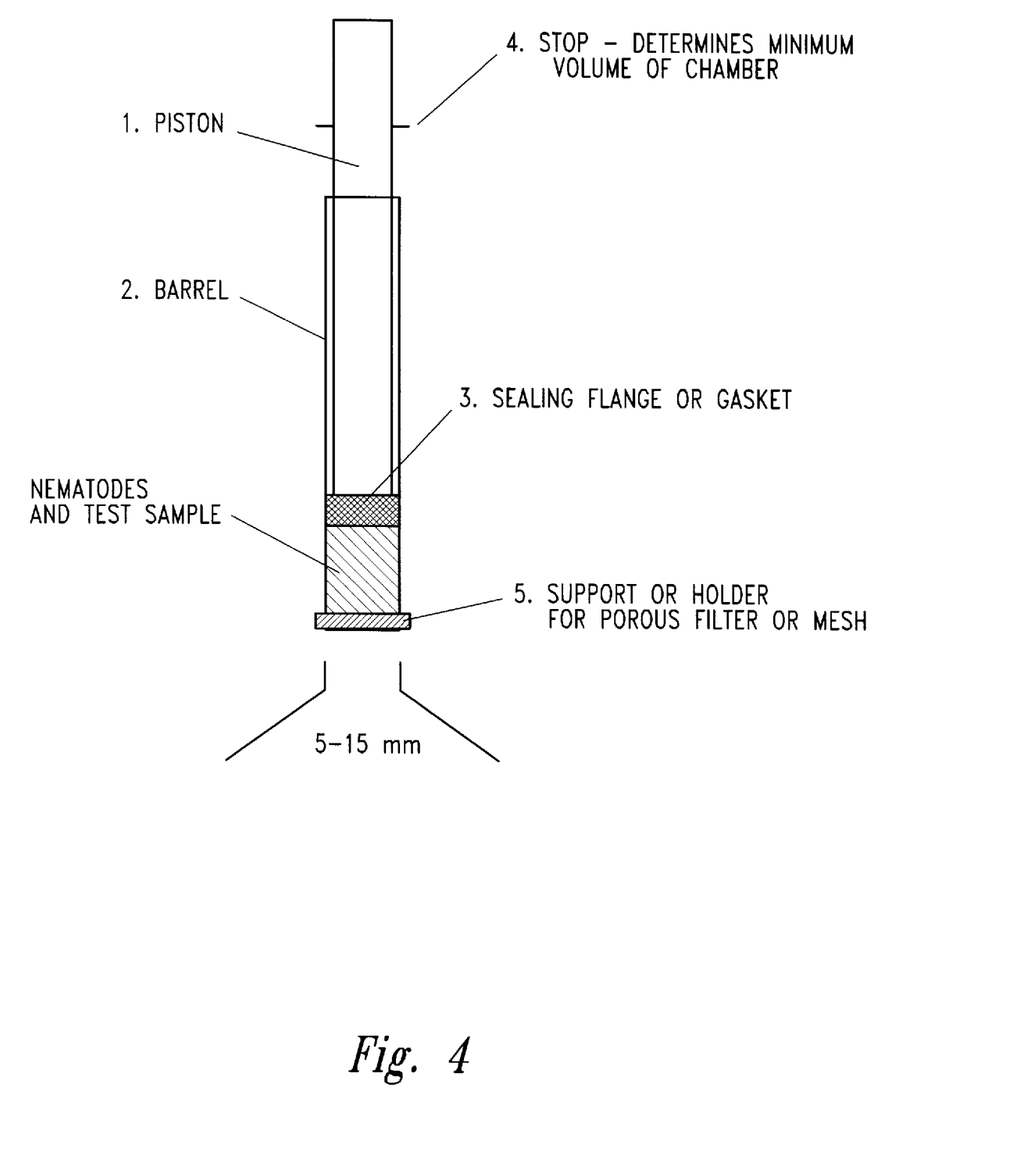
FIG. 4. Self-contained biological testing chamber (STC) for measuring the activity of the reporter genes in the biomonitor.
Figure 5A:
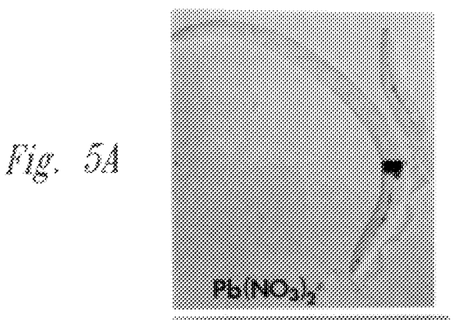
FIGS. 5A–5G. Tissue distribution of β-galactosidase activity in transgenic nematodes exposed to various chemical stressors as detected by Xgal staining (11). All larvae were exposed to each agent for a period of 24 hours. Starting from the top left corner and proceeding clockwise, the concentrations were: 10 mg/L $Pb(NO_3)_2$, 5 mg/L $HgCl_2$, 10 mg/L $CuCl_2$, 100 mM $CdCl_2$, 1 mM paraquat, 100 mM $NaAsO_2$, and 1 mg/L $ZnCl_2$.
Figure 5B:
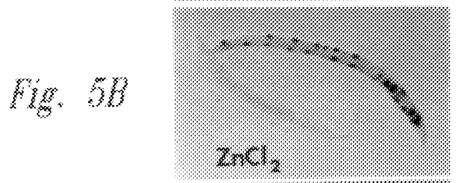
Figure 5C:
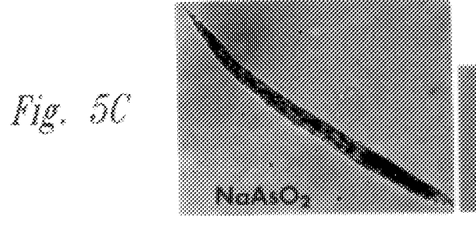
Figure 5D:
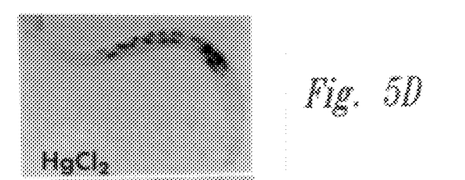
Figure 5E:
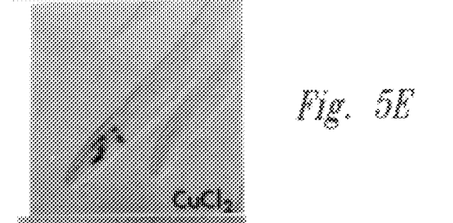
Figures 5F, 5G:
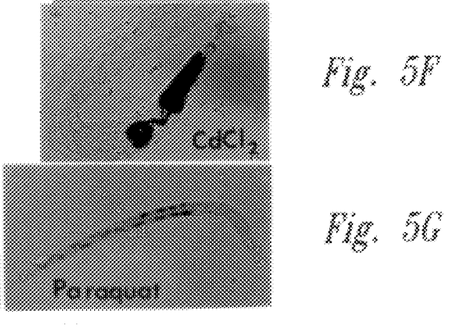

A chamber has been developed in which the animals can be stored, exposed to the test substance, and assayed without the need for pipeting or centrifugation. This greatly simplifies the procedure, and may make it possible to use the biomonitor in field testing. A diagram of one possible manifestation of the test chamber is shown in FIG. 4. This diagram is provided as a further guide to the practitioner of ordinary skill in the art, and is not to be construed as limiting the invention in any way.

Material specifications

The barrel (2) should be transparent (clear plastic or glass), and ideally graduated in milliliters; the filter on the end of the barrel (5) should retain nematodes from early larval stages onwards, but allow passage of liquids and small particles such as bacteria: a 5–10 micron mesh is suitable. All materials should be resistant to acetone and similar solvents.

Functioning of the test chamber

The assembly acts like a syringe—The piston can be drawn upwards or downwards, to draw in or expel liquids, respectively. To set up the system, nematodes are added to the barrel and the piston is inserted and pushed down to the level of the Stop (4). The animals can be stored in this assembly in various forms (see below) until used. The chambers are stored upright in a suitable rack or tube, such that the nematodes settle on the mesh and thereby are in close contact with oxygen in the air, which is essential to maintain their viability.

To expose the nematodes to a liquid test sample, the culture fluid is expelled, and the sample is drawn in, perhaps rinsing once or twice with the test sample. The desired volume of the test sample is drawn in , and the nematodes are incubated for the desired period of time.

Read-out of the level of stress-induced enzyme activity is carried out in the same apparatus, by expelling the test sample and drawing in the appropriate assay solutions in turn. For a colorimetric assay, color intensity can be estimated through the transparent barrel, or the assay solution can be expelled for measurement in a spectrophotometer.

Method of Operation:

The test chamber (FIG. 4) contains a pre-determined number of nematodes at a specific stage of development (egg, L1, L2, L3, L4, dauerlarve or adult) in a nutrient medium (Storage Medium, SM).

1. Test samples, consisting of water samples or aqueous extracts of soils, etc. are suitably diluted and mixed with a concentrated stock solution of SM to give a standard final concentration of the medium.

2. The sample is drawn into the chamber, and the chamber is incubated for the desired time at a standard temperature, usually between 15° and 22° C.

3. The sample is expelled, the chamber is rinsed with a simple salts medium or with water, and the rinse solution is expelled. The nematodes are retained in the chamber by the porous filter or mesh.

4. The nematodes are made permeable to the assay components. A suitable treatment is to draw in acetone and incubate at ambient temperature for a few minutes.

5. The acetone is expelled and the assay solution is drawn into the chamber.

6. The assay results are read after a suitable incubation time, ranging from a few minutes to overnight, at a temperature ranging from ambient to 37° C. Two types of assay have been employed: a qualitative histochemical assay which indicates which tissues have undergone the stress response, and a quantitative soluble assay which provides a colour change reflecting the level of stress-induced enzyme in the whole animal.

III. DETAILED DESCRIPTION OF SPECIFIC EMBODIMENTS OF THE BIOMONITORING SYSTEM

Previous biomonitoring systems have consisted in monitoring some physiological parameter of a wild-type organism such as a microorganism, an invertebrate (mussels, clams, Daphnia) or a vertebrate (usually a fish species) during or after exposure to some test condition. The endpoint of the assay is often lethality, e.g. the LD50 of the test substance is determined (13,14). Other assays have involved measurements of behavior such as movement of fish away from test samples (15), or frequency of pumping in bivalves such as mussels (16); in these cases, complex and expensive electronic equipment forms part of the system. Alternatively, and more recently, the levels of specific biomolecules, usually proteins, in the test species have been measured, e.g. the current interest in measurements of stress proteins (17). The latter assays, while using relatively simple equipment, nevertheless are very time-consuming, involve many manipulations, and require extensive training and experience. They are not suited to use in the field.

The present approach utilizes specially designed transgenic organisms which respond to stressors by producing an easily quantified enzyme which is not normally produced by those organisms. Furthermore, by utilizing the small, easily manipulated nematode, *C. elegans,* readout of the results can be carried out rapidly and simply in the intact organism, without the necessity of disruption of tissues or extraction of the enzyme to be measured. The assay can be performed easily in the laboratory or in the field, by personnel with minimal training.

Advantages of the system:

A. Quantitative or qualitative measures of stress in a multicellular animal.

B. Is responsive to both organic and inorganic stressors.

C. Can be used on all types of samples; fresh or salt water samples, mill effluents, leachaios, sludges, soil elnates, soils or sediments, specific chemicals or mixtures of chemicals.

D. May be carried out in the laboratory or in the field.

E. Readout requires minimal equipment and consists of an easily observable, stable colour change.

F. Following exposure of the organisms to the test sample, results of the stress assay are available within minutes to hours, depending on the magnitude of the imposed stress.

G. The test can be carried out with small sample volumes, i.e. less than 2 mL.

H. The test organism is cheap to grow and maintain.

I. System can be used for monitoring both chronic and acute toxicity.

J. System is more sensitive than current existing lethality tests using wild-type nematodes.

K. System provides information on tissue specificity of the stress response.

Storage of the nematodes:

Three methods of storage of the nematodes directly in the test chamber are possible: i) The animals may be kept in the refrigerator (near 4° C.) for several days before use, as this temperature greatly slows their development. ii) *C. elegans* has a stage called the dauerlarva, which forms when cultures are starved. The dauerlarva does not feed, and can survive for up to three months at ambient temperature, then resume its development when presented with food. Thus the biomonitor strains could be stored in the test chambers as dauerlarvae for up to three months until used: the animals could be fed for 8 hours or so to convert them to normal L4 larvae prior to use in tests. iii) *C. elegans* L1 and L2 larvae can be frozen and stored indefinitely at dry ice or liquid nitrogen temperatures. They could therefore be stored frozen and shipped directly in the test chamber: it would then only be necessary to change the medium and feed the nematodes for a few hours prior to their use in tests.

IV. EXAMPLES

The invention can further be understood by reference to the following examples. The examples presented below are provided as a further guide to the practitioner of ordinary skill in the art, and are not to be construed as limiting the invention in any way. The examples are divided into a) the qualitative assay; b) the quantitative assay; c) use of the self-contained chamber; d) other assays.

a) Qualitative in situ assays. The x-gal staining procedure is described in Fire et al. (3). Nematodes were exposed to the stressing chemical in test tubes or in multiwell disposable plastic dishes, then stained with the histological stain, X-gal, following permeabilization with acetone. The standard reference stress condition, a heat shock at 33° C. was usually carried out with the animals on a Petri plate containing nutrient agar. The tissue staining pattern was observed under a low power binocular microscope. A heat shock for as short a time as 15 min. at 33° C. causes β-galactosidase to be made in most tissues of the animals (4). In addition, various chemical stressors, including heavy metals such as arsenite, cadmium, copper, lead, mercury and zinc, and the herbicide, paraqual, were found to activate the reporter gene after exposures of several hours to 2 days (11, FIG. 5). These agents yield different tissue patterns of stress induction; mercury and paraqual induce only intestinal expression, lead affects pharyngcal muscle, especially at the base of the terminal bulb, copper induces in neurons and muscle at the anterior end of the pharynx, and cadmium throughout the pharynx or occasionally in the intestine. Arsenite exposure produces the most tissue general expression, in a manner reminiscent of classic heat shock induction. These results, illustrated in FIG. 5, suggest that classification of stress agents in complex mixtures may be a useful feature of this biomonitoring system. It is important to note that no staining is seen in nematodes which are not exposed to stressors, i.e. kept in normal culture medium (11).

b) Quantitative assays: In these experiments, nematodes were exposed to the stressor as in a), then permeabilized and assayed using ONPG (α-nitrophenyl-β-D-galactopyranoside), a β-galactosidase substrate which yields a soluble yellow product upon reaction with the enzyme. One version of this standard β-galactosidase assay is described by Rosenthal (18), and its previous use with *C. elegans* by Fire (19). Each assay used approximately 200–15,000 nematodes, depending on the experiment.

Figure 6:
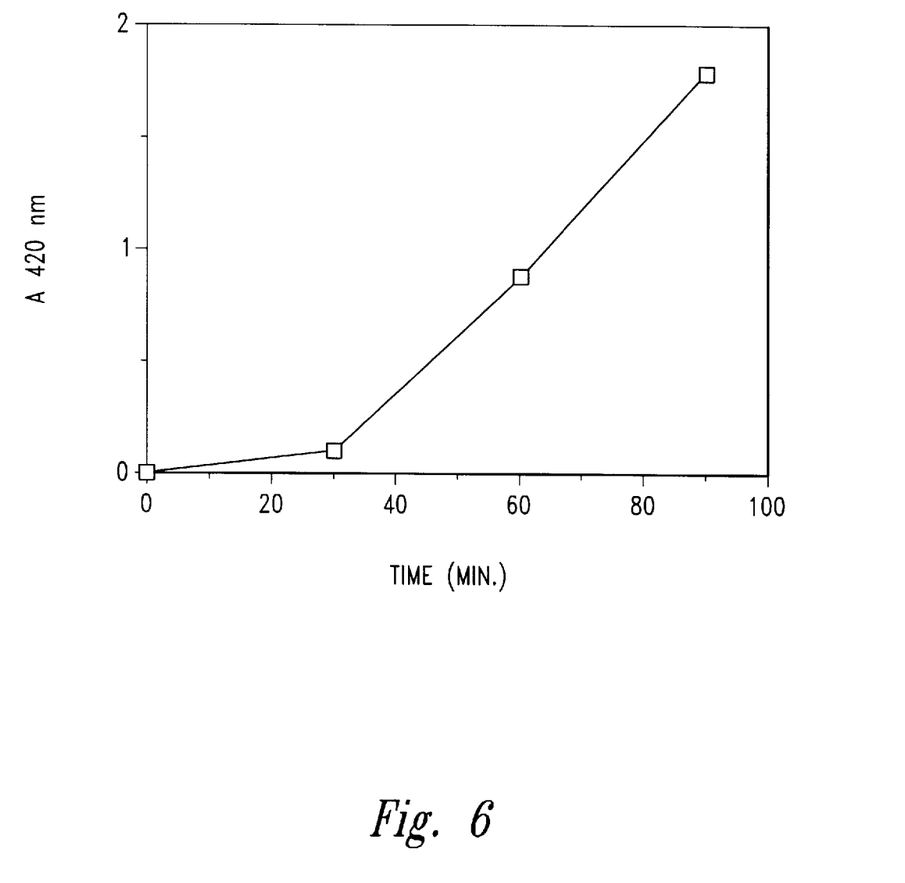
FIG. 6. Quantitative ONPG assay of β-galactosidase activity in PC73 worms following heat shock for various times.

To determine if the enzyme activity produced was proportional to the magnitude of the stress, aliquots of nematodes were heat shocked at 33° C. for various times. The plot shown in FIG. 6 demonstrates that the enzyme activity induced was linear with respect to the length of the heat stress, from 30 min. to the end of the experiment, at 90 min. This experiment indicates that the soluble ONPG assay is sufficiently sensitive and provides a quantitutive measure of heat stress.

Figure 7:
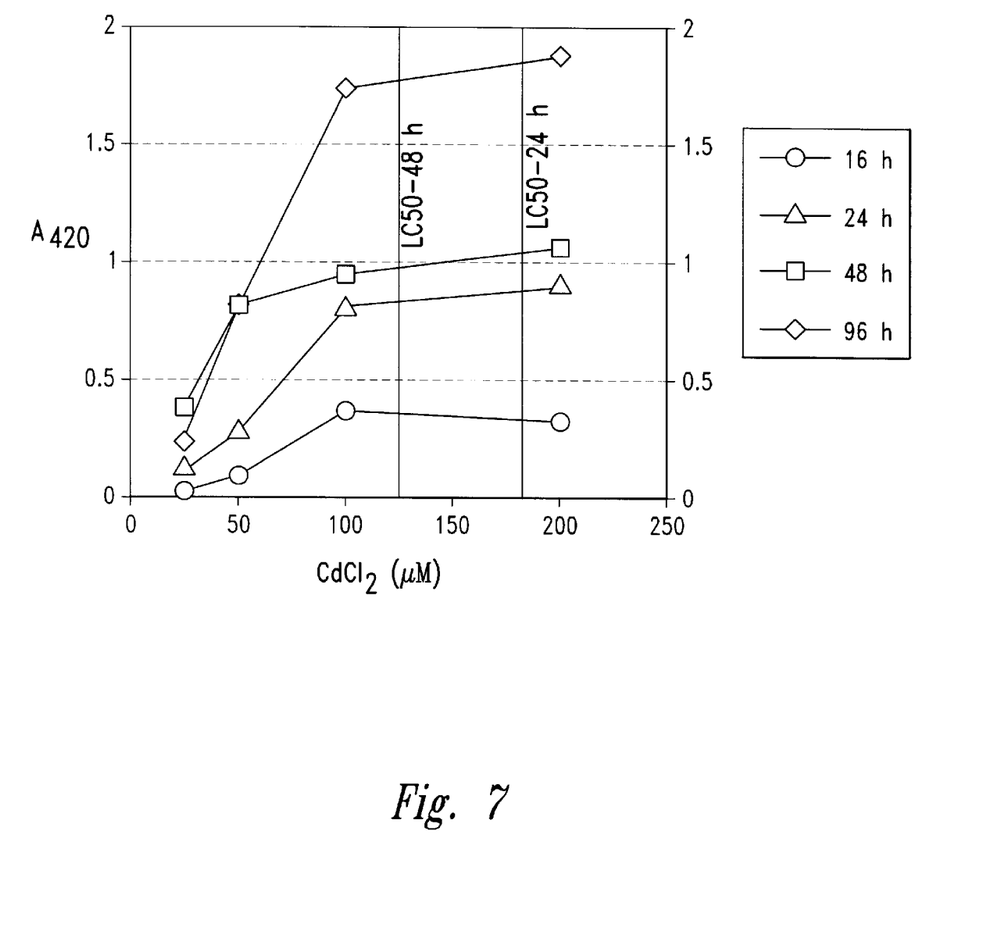
Figure 8:
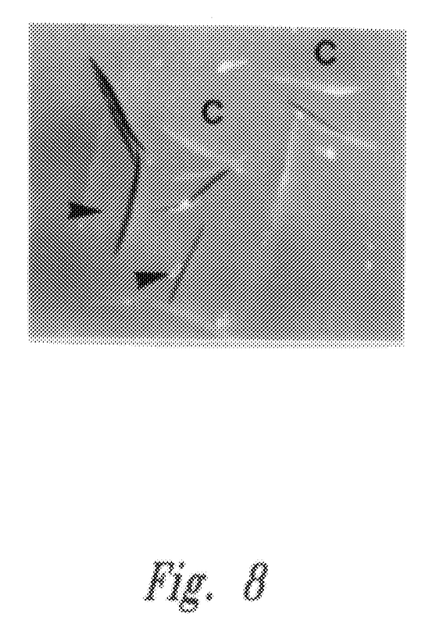

Subsequent experiments have used this assay to measure the effects of chemical stressors (11). The result of an experiment in which nematodes were exposed to cadmium chloride for varying periods of time is shown in FIG. 7.

c) The self-contained test chamber (STC). Prototype STCs were constructed from disposable plastic syringes, or from a syringe plunger and a section of glass tubing as the barrel. Several hundred nematodes were placed inside, the plunger replaced, and the whole assembly was subjected to a heat shock; a control STC was kept at room temperature. After the incubation, all steps of the ONPG assay were carried out directly in the STC. The result was similar to that seen when the assays were done in tubes or wells: room temperature controls showed no colour development, while the heat shocked sample developed an intense yellow colour within 10 min. to several hours depending upon the extent of the heat shock and the number of animals used.

d) Other assays. Since the nematodes can be made permeable to small molecules in general by treatment with certain solvents such as acetone, theoretically any enzyme present in the animals, and which can be measured using low molecular weight substrates, could be used in the above applications. For example, dehydrogenases such as α-glycerophosphate dehydrogenase, normally present in wild-type *C. elegans,* have been measured using a histochemical stain specific for each enzyme, as shown in FIG. 8. Therefore the apparatus and assay methods described here could be used to detect other potential reporter enzymes in suitably engineered transgenic strains, or even naturally occurring nematode enzymes, the activity of which might be indicators of environmental conditions.

Molecules such as bacterial or firefly luciferase could be used as reporters in combination with the hsp16 promoters (7). Other potential regulatory sequences might include promoters inducible by heavy metals, such as those of the metallothionein genes, the cytochrome P450 promoter, or promoters responsive to oxidative stress or to specific toxins.

V. CONCLUSION

This application describes a system for monitoring stress in a living organism. The system consists of:

1. Transgenic strains of the nematode, *Caenorhabditis elegans,* which respond to certain environmental conditions by synthesizing readily detectable enzymes;
2. Methods and compositions for exposing the animals to various aqueous solutions, slurries, soils and sludges,
3. Methods and compositions for measuring the enzymes directly in the animal.

The advantages of this system over other currently available biomonitors are its simplicity, rapidity, relatively low cost, ease of quantitation and tissue specificity of the response, its response to sublethal conditions, its selectivity for certain stressors, and its portability.

A number of logical extensions of this system can be envisaged:

Other reporter genes besides the β-galactosidase used to date, could be used to advantage in the same way, and these could be controlled by and desired promoter.

Enzymes already present in the natural, wild-type organism could be measured, if some are found to be selectively activated or produced in response to changes in environmental conditions.

Other free-living nematode species, such as *Caenorhabditis briggsae* or *Panagrellus redivivus* could be used; *P. redivivus* in particular might present certain advantages, such as lower oxygen requirements for growth or survival, or greater ease of storage.

Creation of sentinel transgenic organisms from other phyla using stress-inducible promoters and reporter gene sequences.

Variations in the design of the self-contained apparatus might include a suction bulb for aspirating samples into the chamber, instead of a piston; flow-through cells with a retaining mesh or porous plug at each end, for placement in flowing water; multiwell plates in which the nematodes are retained in the wells by an overlying porous filter or mesh.

References

1. Sanders, B. M. "The role of stress protein response in physiological adaptation of marine molluseg". Mur. Environ. Res. 24, 207–210 (1988).

2. Sanders, B. M. "Stress proteins: potential as multitiered biomarkers. In Biological markers of environmental contamination", ed. J. McCarthy and L. Shugart. CRC Publishers, Boca Raton, Fla. 135–61 (1990).

3. Sanders, B. M., Martin, L. S., Nelson, W. G., Phelps, D. K. and Welch, W. "Relationships between accumulation of a 60 kDa stress protein and scope-for-growth in *Mytilus eduits* exposed to a range of copper concentrations". Mar. Environ. Res, 31,81–97 (1991).

4. Stringham, E. G., Dixon, D. K., Jones, D. and Candido, E. P. M. "Temporal and Spatial Expression Patterns of the Small Heat Shock (hsp16) Genes in Transgenic *Caenorhabditis elegans*". Molec. Biol. Cell 3, 221–233 (1992).

5. Russnak, R. H. and Candido, E. P. M. "Locus encoding a family of small heat shock genes in *Caenorhabditis elegans*: two genes duplicated to form a 3.8-kilobase inverted repeat". Mol. Cell. Biol. 5(6), 1268–1278 (1985).

6. Jones, D., Russnak, R. H., Kay, R. J. and Candido, E. P. M. "Structure, expression, and evolution of a heat shock gene locus in *Caenorhabditis elegans* that is flanked by repetitive elements". J. Biol. Chem. 261(26), 12006–12015 (1986).

7. Boylan, M., Pelletier, J. and Meighen, B. A. "Fused bacterial luciferase subunits catalyze light emission in sukaryotes and prokaryotes". J. Biol. Chem. 264. 1915–1918 (1989).

8. Fire, A., White Harrison. S. and Dixon, D. "A modular set of β-galactosidase fusion vectors for studying gene expression in *Caenorhabditis elegans*". Gene 93 189–198 (1990).

9. Stringham, E. G. and Candido, E. P. M. "Targeted single cell induction of gene products in *Caenorhabditis elegans*: a new tool for developmental studies". J. Exp. Zool., in press.

10. Stringham, E. G. and Candido, E. P. M. "Use of transgenic strains of the nematode *Caenorhabditis elegans* as biological monitors of environmental stress". Abstracts to SETAC, 91. pp. 10 (1992), Cincinnati, Ohio.

11. Stringham, E. G. and Candido, E. P. M. "Transgenic hsp16-lacZ strains of the soil nematode *Caenorhabditis elegans* as biological monitors of environmental stress". Submitted.

12. Sulston, J. E. and Brenner, S. The DNA of *Caenorhabditis elegans.* Genetics 77, 95–104 (1974).

13. Hatakeyana, S. Shiraishi, H. and Sugaya, Y. "Monitoring of the overall pesticide toxicity of river water to aquatic organisms using a freshwater shrimp, Paratya compressa improvisa". Chemosphere 22, 229–235 (1991).

14. Giesy, J. P., Rosiu, C. J., Graney, R. L. and Henry, M. G. "Benthic invertebrate bioassays with toxic sediment and pore water". Environ, Toxicol. Chem. 9, 233–248 (1990).

15. Baborowski, M., Raschewski, U. and Kuschan, H. "Method and apparatus for determining water toxicity by the reduction in the length of time fish stay in the area". East German patent DD 252685.

16. Ryaranov, A. V., Krainyukova, A. N. and Vasenko, A. G. "Device for biological estimation of water toxicity". Soviet patent SU 946027.

17. "Sublethal bioassay for environmental quality". World Patent No. WO 9013028.

18. Rosenthal, N. In "Methods in Enzymology", S. L. Berger and A. R. Kimmel, eds., Academic Press, 152, 704–720 (1987).

19. Fire, A. "Integrative transformation of *Caenorhabditis elegans*". EMBO J. 5, 2673–2680 (1986).

The embodiments of the invention in which an exclusive property or privilege is claimed are defined as follows:

1. A transgenic nematode selected from the group consisting of PC71, deposited as ATCC Accession Designation No. 209318, PC72, deposited as ATCC Accession Designation No. 209319, and PC73, deposited as ATCC Accession Designation No. 209320, said nematode having a gene construct stably integrated into its genome, and gene construct comprising the nematode hsp16 promoter operably linked to the lacZ gene, wherein the lacZ gene is expressed when said nematode is exposed to a toxin.

2. The transgenic nematode of claim 1 wherein said nematode is PC71.

3. The transgenic nematode of claim 1 wherein said nematode is PC72.

4. The transgenic nematode of claim 1 wherein said nematode is PC73.

5. A kit comprising:
    (a) a test chamber containing a liquid growth medium and at least one transgenic nematode selected from the group consisting of PC71, deposited as ATCC Accession Designation No. 209318, PC72, deposited as ATCC Accession Designation No. 209319, and PC73, deposited as ATCC Accession Designation No. 209320, said nematode having a gene construct stably integrated into its genome, said gene construct comprising a nematode hsp16 promoter operably linked to the lacZ gene, wherein the lacZ gene is expressed when said nematode is exposed to a toxin; and
    (b) means for detecting expression of the lacZ gene.

6. The kit according to claim 5 wherein said kit is used with a sample that is an environmental sample selected from the group consisting of water, soil and sludge.

7. The kit of claim 5 wherein said nematode is PC71.

8. The kit of claim 5 wherein said nematode is PC72.

9. The kit of claim 5 wherein said nematode is PC73.

* * * * *